United States Patent [19]
Rebrovic

[11] Patent Number: 5,883,269
[45] Date of Patent: Mar. 16, 1999

[54] METHOD FOR CONTROLLING THE REACTIVITY OF AN OZONIZATION REACTION PRODUCT

[75] Inventor: Louis Rebrovic, Ross, Ohio

[73] Assignee: Henkel Corporation, Gulph Mills, Pa.

[21] Appl. No.: 767,651

[22] Filed: Dec. 17, 1996

[51] Int. Cl.$^6$ .......................... C01B 15/022; C07C 51/16
[52] U.S. Cl. ................. 549/431; 562/6; 562/524
[58] Field of Search ...................... 562/524, 6; 549/431

[56] References Cited

U.S. PATENT DOCUMENTS

| | | | |
|---|---|---|---|
| 2,813,113 | 11/1957 | Goebel et al. | 562/524 |
| 5,292,941 | 3/1994 | Kigawa et al. | 562/544 |

FOREIGN PATENT DOCUMENTS

| | | |
|---|---|---|
| 294957 | 11/1993 | Japan . |
| 5-294957 | 11/1993 | Japan . |

OTHER PUBLICATIONS

Davis et al., Principles of Chemistry, Saunders College Publishing, p. 485, 1938.
The Peroxide Species Generated by Ozonolysis of Oleic Acid or Methyl Oleate in a Carboxylic Acid Medium, Reborovic, JAOCS, vol. 69, No. 2 (Feb. 1992).
Structures of Ozonolysis Products of Methyl Oleate Obtained in a Carboxylic Acid Medium, Nishikawa et al., JAOCS, vol. 72, No. 6 (1995).

*Primary Examiner*—Gary Geist
*Assistant Examiner*—Rosalynd Keys
*Attorney, Agent, or Firm*—Ernest G. Szoke; Wayne C. Jaeschke; Daniel S. Ortiz

[57] ABSTRACT

A method for controlling the reactivity of an ozonized reaction mixture formed by ozonizing an unsaturated compound, wherein the reactivity of the ozonized reaction mixture is controlled by introducing a reactivity controlling amount of a saturated fatty acid into the reaction mixture before contact with the ozone.

11 Claims, 4 Drawing Sheets

METHOD FOR CONTROLLING THE REACTIVITY OF AN OZONIZATION REACTION PRODUCT

BACKGROUND OF THE INVENTION

It is known that carboxylic acids can be prepared by ozonization of unsaturated compounds followed by reaction of the ozonized material with oxygen at an elevated temperature, optionally in the presence of a catalyst to form the carboxyl group.

RELATED ART

The processes are particularly useful for forming dicarboxylic acids from unsaturated carboxylic acids and unsaturated carboxylic acid esters. The details of such processes are set out in U.S. Pat. No. 2,813,113 to Goebel et al. and U.S. Pat. No. 5,292,941 to Kigawa et al., the contents of which are incorporated herein by reference. Japanese Patent Application No. 4-124311, filed Apr. 17, 1992, published as Japanese Patent Publication 5-294957 on Nov. 9, 1993, discloses a process for producing an ozonization product with reduced reactivity by ozonization of an unsaturated carboxylic acid ester with limited amounts of carboxylic acids present.

Ozonization of ethylenically unsaturated compounds can be conducted in the presence of a diluent to provide a reaction mixture with a low viscosity. For ease of operation, ozonization of unsaturated carboxylic acids or esters of unsaturated carboxylic acids is generally carried out in the presence of a saturated carboxylic acid or an ester of a saturated carboxylic acid as a diluent. Preferably, the saturated carboxylic acid or ester thereof is a product of the process.

The ozonization reaction product is a complex mixture which is dependent upon the unsaturated starting material and the diluents, if any, which are present in the mixture which is ozonized. The articles THE PEROXIDE SPECIES GENERATED BY OZONOLYSIS OF OLEIC ACID OR METHYL OLEATE IN A CARBOXYLIC ACID MEDIUM, Louis Reprovic, JAOCS, vol. 69, No. 2 (February 1992) and STRUCTURES OF OZONOLYSIS PRODUCTS OF METHYL OLEATE OBTAINED IN A CARBOXYLIC ACID MEDIUM, Naoki Nishikawa, et al., JAOCS, vol. 72, No. 6 (1995) disclose the ozonization products which appear in the largest quantities in the ozonization reaction mixture. The articles disclose that the ozonization reaction mixture generally contains the following compounds in various proportions:

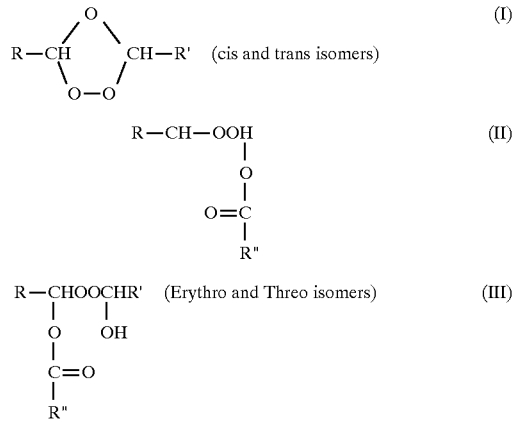

In the structures (I), (II), and (III) the groups R, R' and R" represent groups present in the unsaturated compound or saturated carboxylic acid diluent present in the reaction mixture which is to be ozonized.

The ozonized compounds have different rates of reaction and decomposition. Compound (I) reacts much slower than compounds (II) and (III). It would be useful, if the composition of the ozonization reaction mixture could be controlled, to either reduce the time the mixture must be contacted with oxygen to form carboxyl groups or provide a less reactive and more stable mixture.

SUMMARY OF THE INVENTION

According to the present invention, the reactivity of the ozonization reaction mixture can be controlled by using a saturated carboxylic acid diluent in a reactivity controlling amount, the carboxylic acid diluent having a chain length selected to provide an ozonization reaction mixture with a required reactivity.

The invention comprises a method for controlling the reactivity of an ozonization reaction mixture formed by ozonization of ethylenically unsaturated compounds and particularly an unsaturated fatty acid, an ester of an unsaturated fatty acid or mixtures thereof, which comprises: contacting a mixture of the ethylenically unsaturated compound, the unsaturated fatty acid, the unsaturated fatty acid ester or mixtures thereof to be ozonized and a reaction mixture reactivity controlling amount of a saturated fatty acid or a mixture of saturated fatty acids having a chain length selected to provide an ozonized mixture with required reactivity, with ozone at a temperature of from about −40° C. to about 50° C. Applicants have discovered that reducing the chain length of the saturated fatty acid diluent increases the reactivity of the ozonated reaction mixture. The reactivity of the mixture can be controlled by adjusting the chain length of the saturated carboxylic acid diluent or mixtures of saturated carboxylic acids to obtain a reaction mixture with the required reactivity.

DETAILED DESCRIPTION OF THE INVENTION

Figure 1:
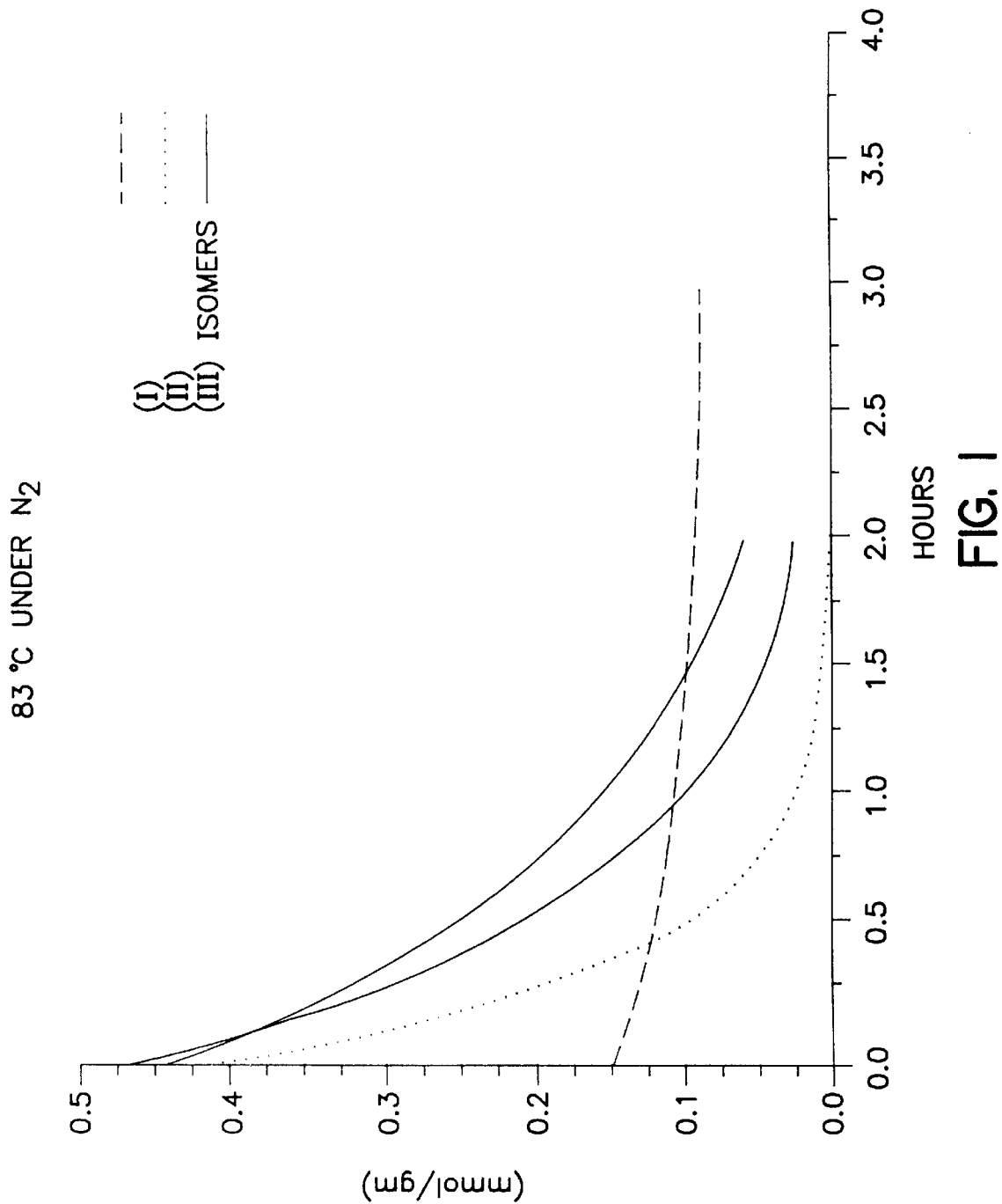
FIG. 1 is a plot of the concentration of the ozonide components in an ozonized mixture with time when held at 83° C. and contacted with nitrogen.

The term "reactivity" as used herein means the rate at which the ozonated reaction products decompose and react to form a carboxyl group. The reactivity of the ozonated reaction mixture is controlled by adjusting the amount and chain length of a saturated carboxylic acid used as a diluent in the reaction mixture. It is known that the reactivity of compounds (II) and (III) is much higher than the reactivity of compound (I). Applicants have discovered that the sum of the amount of compounds (II) and (III) in the ozonized reaction mixture increases as the chain length of a saturated fatty acid diluent is decreased. That is, the total of the amount of compounds (II) and (III) can be increased or decreased by adjusting the amount and chain length of the saturated fatty acid diluent present in the reaction mixture. Using equal weights or volumes of saturated fatty acid diluent, the shorter chain length acids provide more reactive reaction products.

The ozonization process is generally carried out by contacting a mixture comprising an unsaturated fatty acid, unsaturated fatty acid ester or other ethylenically unsaturated compound or mixtures thereof and a diluent with a gas stream which comprises oxygen and ozone under conditions wherein the reaction temperature is maintained from about −40° C. and about 50° C. and preferably from about 10° C. to about 45° C. Lower reaction temperatures provide ozonated reaction mixtures with lower amounts of unwanted reaction products. The temperature at which the ozonization is carried out is generally a compromise between the ability to provide low temperature cooling and the amount of unwanted reaction products in the ozonated reaction mixture. At a temperature above about 50° C., the process is difficult to control and major amounts of unwanted reaction products are formed. At lower temperatures, it is difficult to provide a reaction mixture with a viscosity sufficiently low that it can be efficiently contacted with the gas mixture comprising ozone and oxygen.

A saturated fatty acid diluent not only controls the reactivity of the ozonized reaction product but also controls the viscosity of the reaction mixture. It is known that the viscosity of an ozonized unsaturated fatty acid or ozonized unsaturated fatty acid ester increases as the amount of unsaturated fatty acid or unsaturated fatty acid ester which has reacted with ozone increases. The saturated fatty acid or saturated fatty acid ester diluent can reduce the viscosity to levels which make operation at temperatures below 10° C. feasible.

The gas comprising ozone and oxygen can contain non-reactive diluent gases. The use of diluent gases provides for a more easily controlled ozonization reaction. Inert gases such as carbon dioxide, or the noble gases such as argon, neon and the like, can be utilized to dilute the ozone-containing oxygen. Generally the ozone containing gas contains from about 0.5 to about 7% by volume ozone, the remainder being oxygen and inert diluent gas. Nitrogen is not a preferred diluent gas since at high concentrations it can form nitrogen-containing compounds in the reaction mixture. However, small amounts of nitrogen diluent in the gas mixture comprising ozone and oxygen can be tolerated.

The unsaturated compound and the saturated fatty acid diluent can be contacted with the ozone-containing gas stream from sub-atmospheric to super-atmospheric pressure. However, due to the cost of fabricating the reaction vessels, pressures in the range of from about atmospheric to about 50 pounds per square inch gauge are preferred.

The ozonization reaction mixture containing the ozonized unsaturated fatty acid or ozonized unsaturated fatty acid ester or mixtures thereof is contacted with oxygen essentially free of ozone to form two carboxyl groups at the position of the unsaturation which had been ozonized. The ozonized unsaturated fatty acid is generally contacted with the oxygen-containing gas stream substantially free from ozone at a temperature of from about 60° C. to about 150° C. and preferably between about 80° C. and about 130° C. and most preferably between about 100° C. and about 125° C. to react with the compounds (I), (II), and (III) to form the carboxyl groups.

Complete decomposition of the ozonide, formed from the unsaturated fatty acid or unsaturated fatty acid ester, and formation of two carboxyl groups by contact with oxygen requires a substantial amount of time. Generally, the prior art teaches that a reaction time in a range of about three to about eight hours is required to substantially react and decompose the ozonide present in the ozonized reaction mixture.

The decomposition of the ozonization product by contact with oxygen at an elevated temperature is generally carried out in a series of reaction zones. The ozonization product is introduced into a temperature-controlled reaction zone and mixed with a body of partially reacted ozonization product. Oxygen, preferably in the form of fine bubbles, is passed through the liquid in the reaction zone to react and decompose the ozonization reaction product. The temperature in the first reactor is generally controlled by a cooling means which removes the heat generated by the reaction.

The partially reacted reaction mixture passes from the first reaction zone to a second reaction zone where additional oxygen, preferably in the form of fine bubbles, is passed through the reaction mixture. The second reaction zone, depending on the amount of reaction which has occurred in the first reaction zone, may require temperature control by cooling or require heating since the partially reacted ozonization product can contain only small amounts of material to be reacted. The number of reaction zones utilized in a particular process is dependent on the reaction time required and the ability to properly control the reaction temperatures. Generally three or more reaction zones are used.

After the ozonization product has been reacted with oxygen at an elevated temperature to form the carboxyl groups, the carboxylic acids are generally separated and the saturated carboxylic acids are recycled in the required chain length range to control the reactivity of the ozonization product.

The present invention has been discussed in relation to ozonization and decomposition of unsaturated fatty acids or fatty acid esters. However, the present invention can be utilized to control the reactivity of ozonization reaction mixtures formed by ozonization of ethylenically unsaturated bonds other than those contained in unsaturated carboxylic acids or esters of unsaturated carboxylic acids.

The process of the present invention finds particular usefulness in the production of dicarboxylic acids by ozonization of unsaturated carboxylic acids or esters of unsaturated carboxylic acids. In particular, the process is particularly useful in preparing azeleic acid by ozonization of a mixture comprising oleic acid and the reactivity controlling saturated carboxylic acids.

In the process of the invention, the reactivity controlling saturated carboxylic acids can be present in the reaction mixture in a weight ratio of ethylenically unsaturated compound, unsaturated carboxylic acid or unsaturated carboxylic acid ester or mixtures thereof to saturated carboxylic acid by weight of from about 5:1 to 1:5. Preferably, the ratio by weight of the ethylenically unsaturated compound, unsaturated carboxylic acid or unsaturated carboxylic acid ester to the saturated carboxylic acid is in the range of from about 4:1 to 1:4 and preferably in the range of from about 2:1 to 1:2.

In addition to the amount of the saturated fatty acid diluent, the amount of the more reactive species (II) and (III) is affected by the chain length of the saturated fatty acid diluent. As the chain length of the saturated fatty acid diluent decreases, the sum of the amounts of the (II) and (III) compounds (the more reactive and more easily decomposed compounds) in the ozonated reaction mixture increases. When equal weights or volumes of the saturated carboxylic acid diluents are present in the mixture to be reacted with ozone, the mixture containing the shortest average chain length saturated carboxylic acid diluent produces the most reactive mixture after ozonization.

As the reactivity of the reaction mixture is increased, by an increase in the amount of the more reactive species, the contact time at the elevated temperature between the ozonized reaction mixture and the oxygen-containing gas can be reduced. The reduction in the reaction time can substantially increase the plant capacity or decrease the size of the reaction vessels required for the oxidation-decomposition of the ozonized reaction product. The increase in the reactivity can be clearly seen from the following examples.

The effect of the chain length of the saturated carboxylic acid was determined as follows: a mixture of 5 grams (17.7 mmol) of oleic acid and 10.0 ml of carboxylic acid solvent (diluent) were added to a modified test tube (a 2.2 cm in diameter, 13 cm long test tube with a two-headed 50 ml round bottom flask fused to the top, a Claisen head with a sparge tube and reflux condenser was mounted on the top of the modified test tube reactor). The reactor containing the reagents was immersed in a 25° C. water bath and an ozone/oxygen gas mixture was bubbled through the reaction mixture at 0.3 mmol $O_3$/minute until the reaction was complete. When the reaction was complete, a sample was taken for HNMR ($CDCl_3$: 10% solution) analysis. The peaks in the NMR analysis of the reaction mixture were analyzed and the compounds assigned according to known procedure. The results of the experiments are shown in Table 1.

tures of acids of different chain lengths can be used to provide a reaction mixture with a required reactivity.

Examples 12 and 13 were carried out to determine the reactivity of the ozonide compounds in the ozonized reaction mixture. In examples 12 and 13, a mixture of 35.0 g of oleic acid and 35.0 g of octanoic acid were added to a modified test tube (2.2 cm diameter, 21.5 cm long test tube with a four head 100 ml round bottom flask fused to the top). The reactor was fitted with a sparge tube and a reflux condenser. The reactor containing the reagents was immersed in a 25° C. water bath and an ozone/oxygen gas mixture was bubbled through the reaction mixture at 1.0 mmol $O_3$/min until the reaction was complete.

A portion of the reaction mixture was placed in a reactor as described in Example 1, and the reactor containing the reaction mixture was immersed immediately in a water bath

TABLE 1

| Example | Chain Length of Solvent $CH_3$-$(CH_2)_x$-$CO_2H$ X | cis/trans 1,2,4-Trioxolane(+) (I) Percent by Weight | 1-Acyloxyalkyl-1-Hydro-peroxide (II) Weight percent | 1-Acyloxyalkyl-1-Hydroxy alkyl peroxide (Erythro + Threo) (III) Weight percent | Total Acyloxy-peroxy (II) + (III) Weight Percent |
|---|---|---|---|---|---|
| 1 | 0 | 3.05 | 52.2 | 32.7 | 84.9 |
| 2 | 1 | 7.14 | 56.4 | 26.8 | 83.2 |
| 3 | 2 | 8.74 | 34.0 | 38.2 | 72.2 |
| 4 | 4 | 10.39 | 28.3 | 40.4 | 68.7 |
| 5 | 6 | 11.76 | 21.4 | 38.2 | 59.6 |
| 6 | 7 | 12.06 | 20.4 | 37.3 | 57.7 |

REBROVIC

Examples 1–6 clearly show that as the chain length of the saturated carboxylic acid diluent decreases, the amounts of the more reactive acyloxyperoxide compounds (II) and (III) in the reaction mixture increase and the amount of the less reactive compound (I) decreases.

Examples 7 through 11 were carried out in a manner similar to Examples 1 through 6, except that in Examples 8, 9 and 10, a mixture of acetic acid and pelargonic acid were utilized as the diluent. The ratio by volume of acetic and pelargonic acid and the amount of reactive species formed during the reaction as determined by HNMR analysis as in examples 1–6 are shown in Table 2.

at 83° C. and oxygen gas or nitrogen gas was passed through the mixture. Samples were taken for analysis by HNMR ($CDCl_3$: 10% solution) and the peroxide content was determined by an iodometric peroxide method. The results of the experiment are shown in FIG. 1, FIG. 2, FIG. 3 and FIG. 4.

FIG. 1 is a plot of the concentration of the major ozonide components in the ozonated reaction mixture against time over which $N_2$ was bubbled through the mixture at 83° C. The acyloxyperoxide compounds (II) and (III) react rapidly and are reduced to low concentrations in a short time. The trioxolane component (I) reacts slowly and its concentration is only slightly reduced after 3 hours.

TABLE 2

| EXAMPLE | VOLUME ACETIC/ PELARGONIC | TOTAL ACYLOXYPEROXY (II) + (III) percent by weight | cis/trans 1,2,4-TRIOXOLANE (I) percent by weight |
|---|---|---|---|
| 7 | 0/100 | 57.7 | 12.06 |
| 8 | 25/75 | 73.0 | 5.81 |
| 9 | 50/50 | 74.8 | 4.16 |
| 10 | 75/25 | 79.3 | 3.94 |
| 11 | 100/0 | 84.9 | 3.05 |

Figure 2:
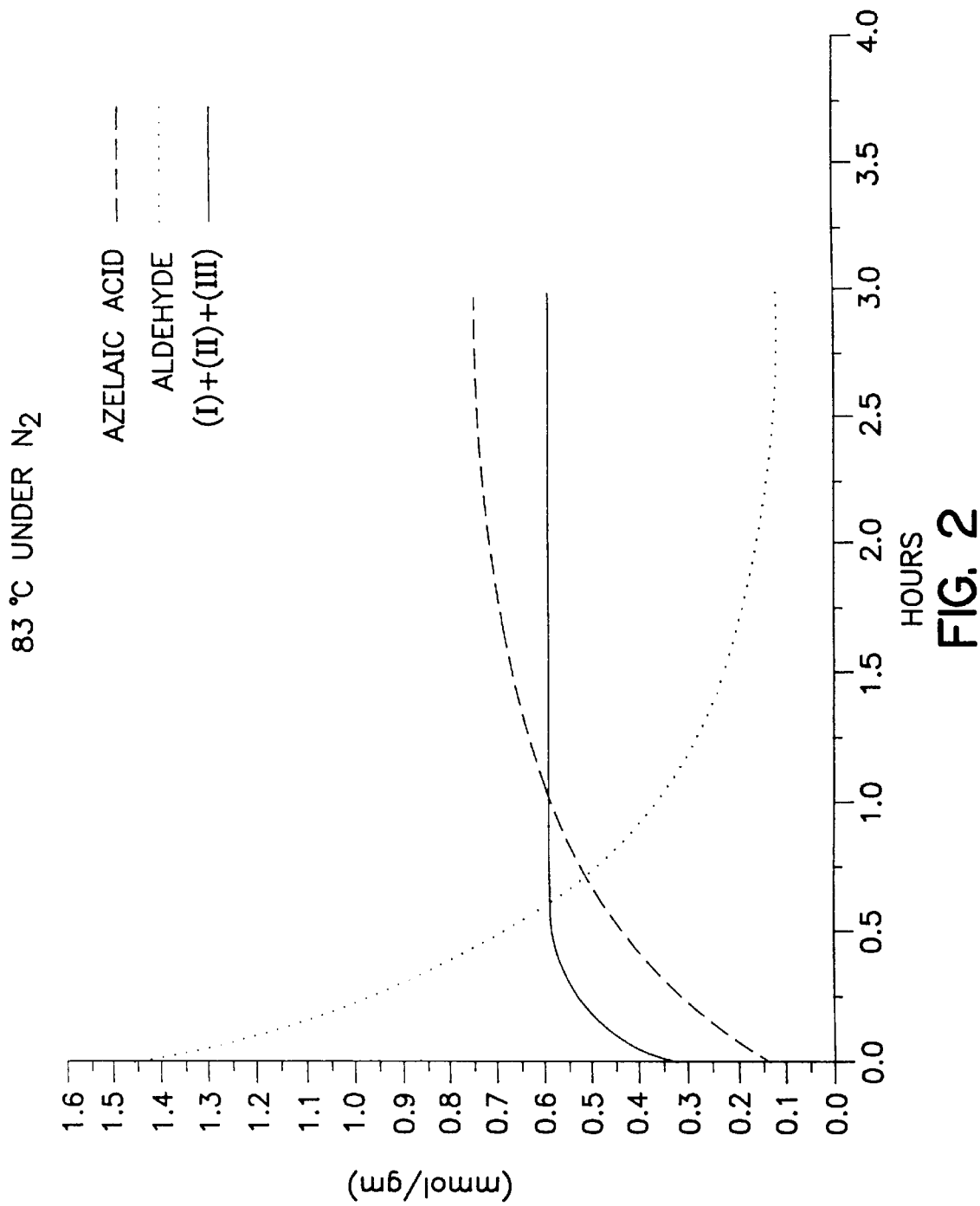
FIG. 2 is a plot of the concentration of ozonide decomposition products in an ozonized mixture with time, when held at 83° C. and contacted with nitrogen.

Table 2 clearly shows that as the ratio of acetic to pelargonic acid is increased, the total amount of the acyloxyperoxy-type compounds (II) and (III) in the reaction mixture increases and the amount of cis/trans 1,2,4-trioxolane (I) decreases. The acyloxyperoxy compounds are substantially more reactive than the 1,2,4-trioxolane compounds. The average chain length of the saturated acid diluent affects the reactivity of the reaction mixture. Mix- FIG. 2 is a plot of the amount of products formed by decomposition of the ozonide and ozonide which remains unreacted in the mixture in the experiment of FIG. 1. Without the presence of oxygen, aldehyde (which co-forms with carboxylic acid) formed by decomposition of the oleic acid ozonide can not react to form a carboxyl group. Carboxylic acid and aldehyde are theoretically formed on a mole for mole basis when the ozonide of oleic acid decomposes. When oxygen is present, the aldehyde group reacts to form a carboxyl group. In the plot of the results of the experiment shown in FIGS. 1 and 2, as the oleic acid ozonide decomposes the amount of azeleic acid, pelargonic acid (NOT SHOWN) and aldehyde increases. As can be seen, the amount of component (I) decreases slowly while components (II) and (III) disappear from the mixture relatively quickly.

Figure 3:
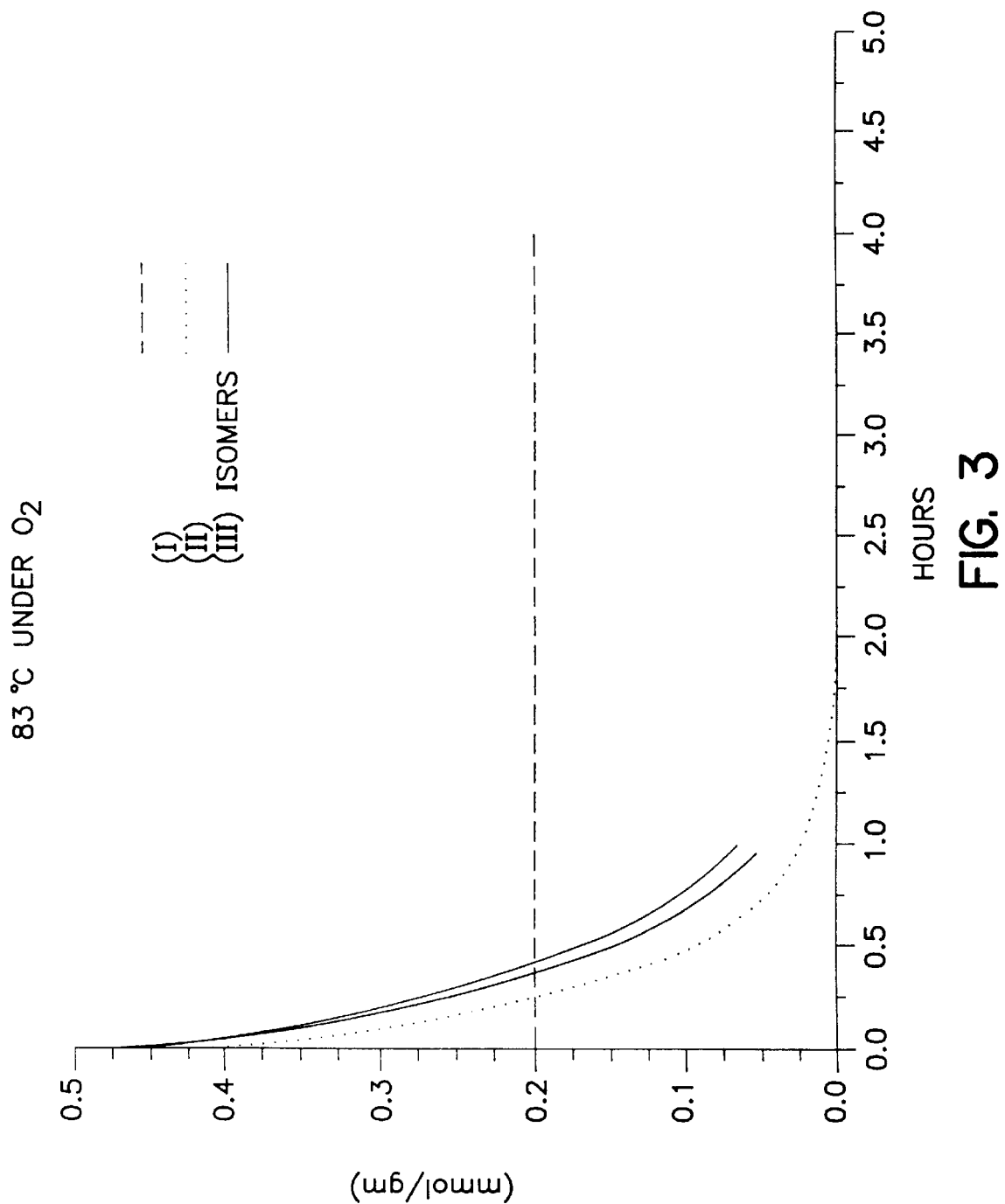
FIG. 3 is a plot of the concentration of the ozonide components in an ozonized mixture with time when held at 83° C. and contacted with oxygen.

FIG. 3 is a plot of the composition of the ozonated reaction mixture of equal volumes of oleic acid and octanoic acid held at 83° C. with oxygen passing through the mixtures against time. The components (II) and (III) in the mixture decompose rapidly while the component (I) in the mixture decomposes slowly. After two hours component (II) has substantially disappeared from the mixture.

Figure 4:
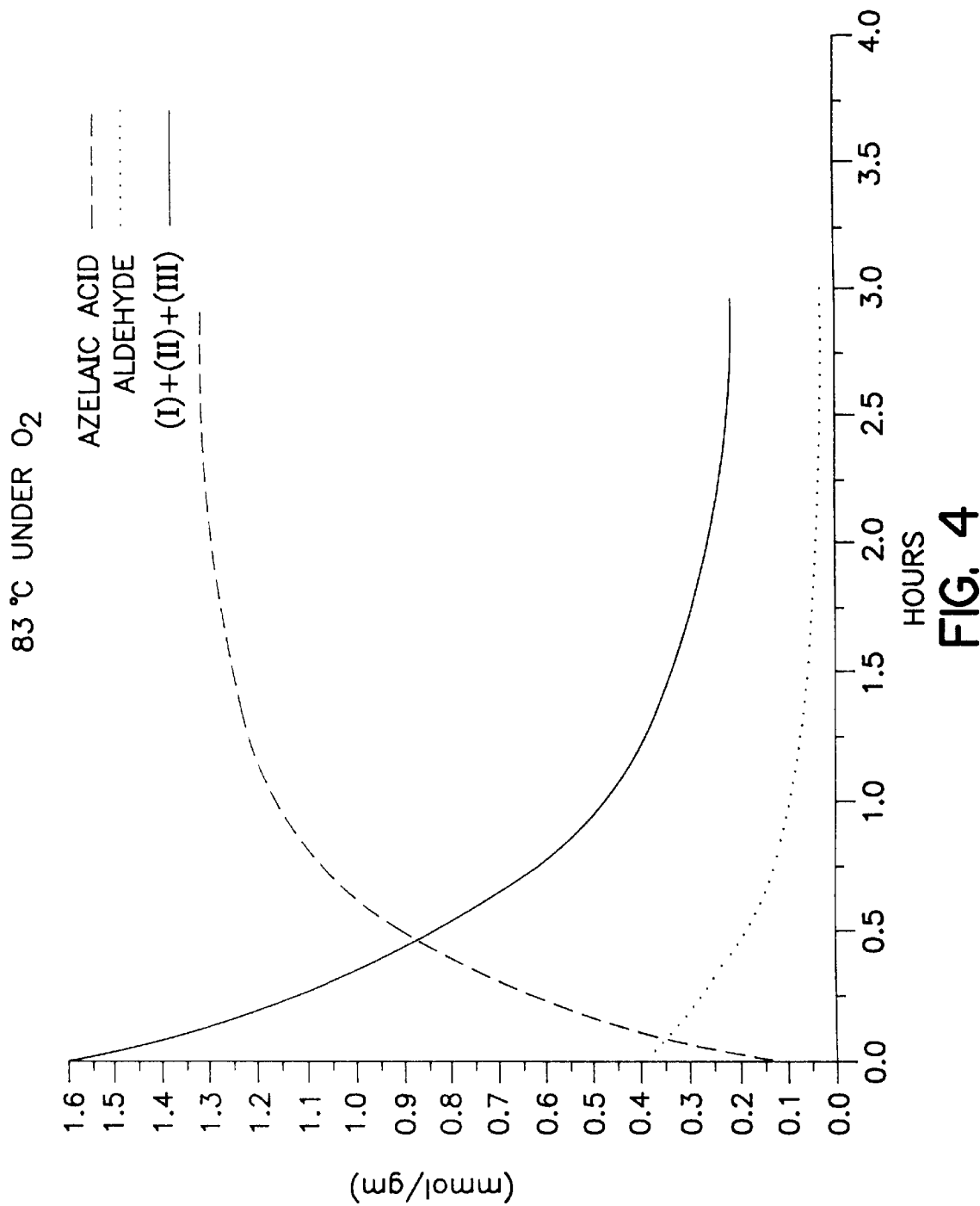
FIG. 4 is a plot of the concentration of ozonide decomposition products in an ozonized mixture with time when held at 83° C. and contacted with oxygen.

FIG. 4 is a plot of the same experiment as shown in FIG. 3, showing the amount of ozonide, azeleic acid and aldehyde in the mixture as a function of time. The concentration of ozonide is rapidly reduced initially. After the components (II) and (III) have been substantially reacted from the mixture, the ozonide is decomposed more slowly as compound (I) reacts. Since oxygen is present, the amount of aldehyde in the mixture remains at a low level when compared to FIG. 2. The amount of azeleic acid reaches a substantially higher concentration when compared to FIG. 2.

At higher temperatures, the decomposition reaction is more rapid. As the concentration of ozonide and aldehyde in the mixture is reduced, it can be advantageous to introduce a catalyst into the mixture to increase the rate of the decomposition reaction and oxidation of the aldehyde.

FIGS. 1–4 show that compounds of the type (II) and (III) are substantially more reactive than compounds of the type (I).

The results of the experiments show that the acyloxyperoxy compounds (II) and (III) are substantially more reactive than the 1,2,4-trioxolane compound (I). FIGS. 1–4 clearly show that the acyloxy compounds are substantially more reactive than the 1,2,4-trioxolane compounds. Since the acyloxy compounds are substantially more reactive than the trioxolane compounds, and the amount of the acyloxy compounds can be controlled by controlling the amount and type of the carboxylic acid diluent, the method of the present invention can be used to control the reactivity of the ozonized reaction mixture.

If the ozonization process provides an ozonized product which is too reactive to be safely handled in a subsequent oxidation process, the reactivity can be reduced by selecting the amount and type of solvent to provide an ozonized reaction mixture with a lower reactivity. Theoretically, the lowest reactivity can be achieved by not using a carboxylic diluent; however, other diluents must be used to provide a reaction mixture which can be effectively contacted with the ozone/oxygen mixture. Use of non-carboxylic acid diluents makes the process more complex and requires additional purification steps. The present invention provides a method for controlling the reactivity of the ozonized reaction mixture using carboxylic acids which are related to or products of the process.

The present invention has been described in relation to ozonization of oleic acid, however, the invention can be applied to ozonization of any ethylenically unsaturated compound in which the double bonds are reacted with ozone in the presence of a diluent material. The amount of the saturated carboxylic acid and the chain length of the saturated carboxylic acid can be utilized to provide an ozonized reaction mixture with a required reactivity. The method of the present invention can also be utilized to lower the reactivity of an ozonization process by utilizing a carboxylic acid diluent having a longer chain length. Saturated carboxylic acids with chain lengths from 2 to about 22 carbon atoms can be utilized as diluents for the process.

I claim:

1. A method for controlling the reactivity of an ozonized reaction mixture formed by ozonization of an unsaturated compound which comprises: contacting a mixture comprising the unsaturated compound to be ozonized and a reaction mixture reactivity controlling amount of a saturated fatty acid diluent, with an ozone containing gas at a temperature of from about −40° C. to about 50° C., whereby the reactivity of the ozonized reaction mixture is controlled by adjustment of the amount and chain length of the saturated fatty acid.

2. The method of claim 1 wherein the unsaturated compound is a fatty acid.

3. The method of claim 2 wherein the fatty acid comprises oleic acid.

4. The method of claim 1 wherein the saturated fatty acid comprises a mixture of saturated fatty acids.

5. The method of claim 1 wherein the saturated fatty acid has from 2 to about 22 carbon atoms.

6. The method of claim 1 wherein the ratio by weight of unsaturated compound to saturated fatty acid is from about 4:1 to about 1:4.

7. The method of claim 1 wherein the ozone containing gas comprises from about 0.5% to about 7% by volume ozone.

8. The method of claim 7 wherein the mixture is contacted with the ozone containing gas at a temperature from about 10° C. to about 45° C.

9. The method of claim 8 wherein the ratio by weight of unsaturated compound to saturated fatty acid is from about 2:1 to about 1:2.

10. The method of claim 1 which further comprises contacting the ozonization reaction mixture with an oxygen containing gas at a temperature from about 80° C. to about 150° C.

11. The method of claim 9 wherein the ozonization reaction mixture is contacted with oxygen at a temperature of from about 100° C. to about 140° C.

* * * * *